United States Patent [19]

Berber et al.

[11] 4,247,783
[45] Jan. 27, 1981

[54] PHOTOELECTRIC CONVERTER OF SIZES OF PARTICLES EMPLOYING CALIBRATION LIGHT PULSES WITH INCREASED STABILITY

[76] Inventors: Viktor A. Berber, ulitsa Shelkovichnaya, 184, kv. 65; Vladimir A. Zolotenko, 2 Detsky proezd, 2, kv. 18, both of Saratov; Evgeny N. Naguev, ulitsa Shevchenko, 62, kv. 55, Smolensk; Vladimir V. Pavlov, ulitsa Sovetskaya, 21, kv. 56, Saratov; Viktor E. Sokolov, ulitsa Shelkovichnaya, 194, kv. 49, Saratov; Alexei N. Syromyatnikov, ulitsa Pushkina, 17/25, kv. 66, Saratov; Anatoly I. Eremenko, 2 Sadovaya, 98, kv. 19, Saratov, all of U.S.S.R.

[21] Appl. No.: 959,248

[22] Filed: Nov. 9, 1978

[30] Foreign Application Priority Data

Jan. 24, 1978 [SU] U.S.S.R. .............................. 2564801

[51] Int. Cl.³ ............................................. G01N 15/02
[52] U.S. Cl. ..................................... 250/574; 356/335
[58] Field of Search ............... 250/573, 574, 575, 576; 356/335, 336, 339, 341, 243; 350/266, 269

[56] References Cited

U.S. PATENT DOCUMENTS

| | | |
|---|---|---|
| 3,045,123 | 7/1962 | Fremmer . |
| 3,127,464 | 3/1964 | Gustavson ...................... 356/243 X |

FOREIGN PATENT DOCUMENTS

| | | |
|---|---|---|
| 1801435 | 4/1970 | Fed. Rep. of Germany . |
| 1598138 | 10/1970 | Fed. Rep. of Germany . |
| 1066499 | 4/1967 | United Kingdom . |
| 1089848 | 11/1967 | United Kingdom . |

OTHER PUBLICATIONS

A. A. Kirsh et al., "Improvement and Calibration of an AZ Jet-Type Photoelectric Aerosol Counter"; Kollaidnyi Zhurnal, vol. 37, No. 4, pp. 778-781; Jul.-Aug.'75.

*Primary Examiner*—David C. Nelms
*Assistant Examiner*—Edward P. Westin
*Attorney, Agent, or Firm*—Fleit & Jacobson

[57] ABSTRACT

A photoelectric converter of sizes of particles contained in a flow of gas to electric pulses comprises a chamber with a means for directing an aerosol flow into and from said chamber optically connected to an illumination means which forms a convergent light flux to illuminate the aerosol flow, and to a photoreceiver arranged so that its optical axis, as well as that of the illumination means and the axis of the aerosol flow all intersect at a right angle inside the chamber. The converter further includes a channel for transmitting part of the light flux of the illumination means to the photoreceiver, and a calibration light pulse former accommodated in said channel. The latter contains two mirrors installed in the chamber across the optical axes of the illumination means and the photoreceiver, respectively, beyond the point of intersection of said optical axes. The calibration light pulse former comprises a diaphragm and a mechanical shutter which comprises, in turn, a rod and a reciprocating drive. The photoelectric converter according to the invention is advantageous over conventional converters in that it increases the stability of calibration light pulses and thus improves the accuracy of measuring the sizes of particles contained in aerosols. In addition, the photoelectric converter of this invention is more reliable and easier to manufacture than those known in the art.

1 Claim, 2 Drawing Figures

PHOTOELECTRIC CONVERTER OF SIZES OF PARTICLES EMPLOYING CALIBRATION LIGHT PULSES WITH INCREASED STABILITY

FIELD OF THE INVENTION

The present invention relates to instrument making and, more particularly, to photoelectric converters of sizes of particles contained in gas flows to electric pulses.

The invention is applicable to the dispersion analysis of aerosols or powders dispersed in the air.

The invention is best applicable to devices for measuring the dust content in the air.

BACKGROUND OF THE INVENTION

When the dispersion analysis of an aerosol is carried out photoelectrically, it is important to determine the size of each particle. The amplitude of electric pulses at the output of the photoelectric converter is proportional to particle sizes and also depends upon the sensitivity of the converter, which varies following changes in the voltage applied to the lamp and photosensitive element, the ambient temperature and other factors.

Variations in the sensitivity of the photoelectric converter lead to changes in the electric pulse amplitudes, which, in turn, accounts for errors in the determination of particle sizes.

In order to increase the accuracy of the dispersion analysis, it is necessary to calibrate the sensitivity of the photoelectric converter.

There is known a photoelectric converter of sizes of particles contained in a flow of gas to electric pulses (cf. "The Photoelectric Particle Counter of the A3-5 Type", SHF Electronics, 1970, Series 10, p. 92 in Russian), comprising a chamber with a means for directing an aerosol flow into and from the chamber which is optically connected to an illumination means forming a convergent light flux to illuminate the aerosol flow, and to a photoreceiver.

The illumination means and the photoreceiver are arranged so that their optical axes and the axis of the aerosol flow all intersect at a right angle inside the chamber. The photoelectric converter under review further includes a channel to transmit part of the light flux generated by the illumination means to the photoreceiver. The latter is a light guide arranged outside the chamber and optically connected thereto. Finally, the photoelectric converter includes a calibration light pulse former comprising a diaphragm installed at the input of the light guide, and a mechanical shutter constructed as a slotted disc. The mechanical shutter is coupled to a rotation drive. The shutter and light guide are accommodated in a common housing.

The channel for transmitting part of the light flux to the photoreceiver is of a complex configuration and great length, whereby it lacks rigidity. This disadvantage accounts for an unstable amplitude of calibration light pulses.

Besides, the use of the rotation drive makes it hard to synchronize the calibration light pulses with electric control pulses produced by the electronic means incorporated in the device for the dispersion analysis of aerosols.

SUMMARY OF THE INVENTION

It is an object of the present invention to improve the stability of the calibration light pulse amplitudes.

It is another object of the invention to make the photoelectric converter of sizes of particles contained in flows of gas to electric pulses more reliable and easier to manufacture.

The foregoing objects are attained by providing a photoelectric converter of sizes of particles contained in a flow of gas to electric pulses, comprising a chamber provided with a means for directing an aerosol flow into and from said chamber which is optically connected to an illumination means forming a convergent light flux to illuminate the aerosol flow, and to a photoreceiver arranged so that its optical axis, that of the illumination means and the axis of the aerosol flow all intersect at a right angle inside the chamber, the photoelectric converter further including a calibration light pulse former accommodated in a channel for transmitting part of the light flux generated by the illumination means to the photoreceiver, and comprising a diaphragm and a mechanical shutter, the photoelectric converter being characterized, according to the invention, in that the channel for transmitting part of the light flux to the photoreceiver includes two mirrors arranged inside said chamber across the optical axes of the illumination means and the photoreceiver, respectively, beyond the point of intersection of said optical axes, and in that the diaphragm and the mechanical shutter are interposed between the mirrors, the mechanical shutter comprising a rod with a reciprocating drive.

The photoelectric converter of sizes of particles contained in a flow of gas to electric pulses in accordance with the invention features an increased stability of calibration light pulses, which accounts for a better accuracy of the dispersion analysis of aerosols. In addition, the photoelectric converter according to the invention is more reliable and easier to manufacture than photoelectric converters of the conventional types.

BRIEF DESCRIPTION OF THE ATTACHED DRAWINGS

Other objects and advantages of the present invention will become more apparent from the following detailed description of a preferred embodiment thereof, taken in conjunction with the accompanying drawings, wherein.

DETAILED DESCRIPTION OF THE INVENTION

The following description refers to a case when the photoelectric converter of sizes of particles contained in a flow of gas to electric pulses according to the invention is employed in a device for dispersion analysis of aerosols.

Figure 1:
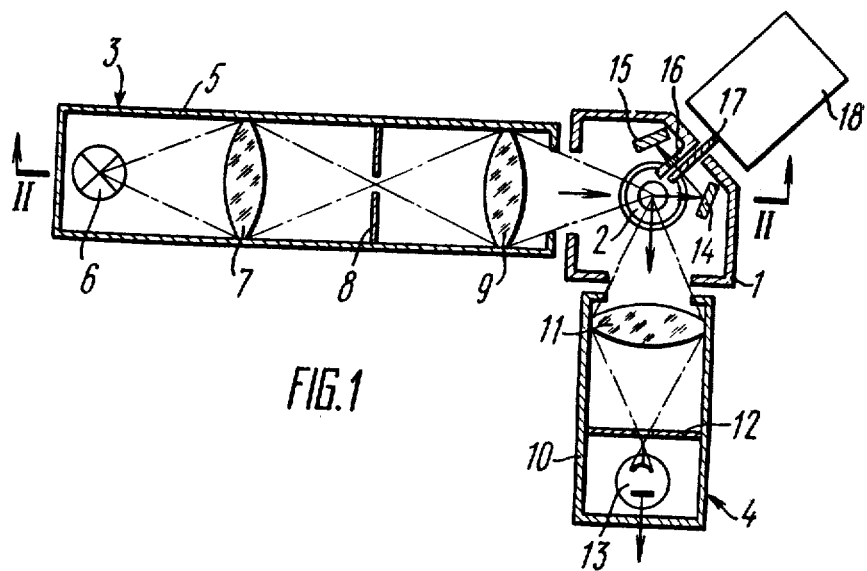
FIG. 1 is a schematic elevation view of a photoelectric converter of sizes of particles contained in a flow of gas to electric pulses, in accordance with the invention.

Referring to the attached drawings, the photoelectric converter comprises a chamber 1 (FIG. 1) provided with a means for driving an aerosol flow into and out of the chamber 1. FIG. 1 shows an outlet pipe 2 of the aerosol flow driving means. The chamber 1 is optically connected to an illumination means 3 which forms a convergent light flux to illuminate the aerosol flow, and to a photoreceiver 4. The chamber 1 screens the aerosol flow introduced therein and the photoreceiver 4 from external light sources. The illumination means 3 and the photoreceiver 4 are so arranged with respect to the chamber 1 that their optical axes intersect the axis of the aerosol flow at right angles inside the chamber 1. The illumination means 3 comprises a housing 5 which accommodates, in successive arrangement, a light source 6, a first converging lens 7, a diaphragm 8, and a second converging lens 9. According to an alternative embodiment, the illumination means 3 comprises a light source 6 with a reflector and a diaphragm; in fact, its function can be performed by any system capable of forming a convergent light flux. The photoreceiver 4 comprises a housing 10 which accommodates, in successive arrangement across the path of the light flux, a converging lens 11, a diaphragm 12, and a photocell 13. According to an alternative embodiment, the photoreceiver 4 is a system of lenses with a diaphragm and a photosensitive element of any type, such as a photoelectron multiplier, photodiode, phototransistor, etc. The photoreceiver 4 is intended to convert light pulses produced by each particle contained in the aerosol flow to electric pulses. A channel for transmitting part of the light flux generated by the illumination means 3 to the photoreceiver 4 comprises two mirrors 14 and 15 arranged in the chamber 1. The mirror 14 is arranged across the optical axis of the illumination means 3. The mirror 15 is arranged across the optical axis of the photoreceiver 4. The two mirrors 14 and 15 are arranged across the above-mentioned optical axes beyond the point of intersection of these axes. A calibration light pulse former positioned in the channel for transmitting part of the light flux to the photoreceiver 4 contains a diaphragm 16 and a mechanical shutter which comprises a rod 17 with a reciprocating drive 18. The rod 17 is shaped as a cylinder, but it may also be shaped as a bar, strip, etc. The diaphragm 16 is interposed between the mirrors 14 and 15 and serves to separate that part of the light flux which is reflected by the mirror 14. The rod 17 is introduced into the chamber 1 and arranged in front of the diaphragm 16, across the light flux reflected by the mirror 14; according to an alternative embodiment, the rod 17 is arranged behind the diaphragm 16.

Figure 2:
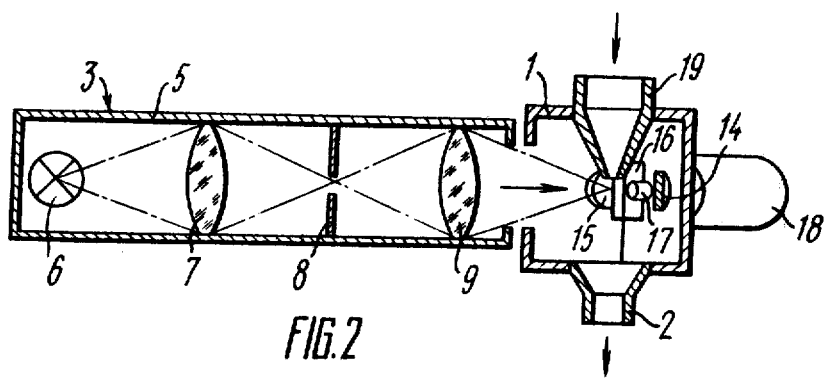
FIG. 2 is a section taken on line II—II of FIG. 1.

Apart from the outlet pipe 2, the aerosol flow driving means includes a cone-shaped nozzle 19 (FIG. 2) intended for aerosol flow shaping. The aerosol flow driving means may be of different designs.

The photoelectric converter of sizes of particles contained in a flow of gas to electric pulses (FIG. 1) operates as follows.

The light flux generated by the light source 6 is converged by the lens 7 in the plane of the aperture of the diaphragm 8. The light flux passed through the diaphragm 8 is converged by the lens 9 in the chamber 1 to illuminate the aerosol flow directed into the chamber 1 through the cone-shaped nozzle 19 (FIG. 2) of the aerosol flow driving means. Some light is scattered by individual particles contained in the aerosol flow as they traverse the convergent light flux of the illumination means 3; this light is converged by the lens 11 in the plane of the aperture of the diaphragm 12. The light flux passed through the diaphragm 12 is received by the photocell 13 to be converted thereby to electric pulses. The light flux of the illumination means 3 is reflected by the mirror 14 and directed through the diaphragm 16 at the mirror 15 which, in turn, direct it to the photoreceiver 4.

The diaphragm 16 separates a predetermined part of the light flux of the illumination means 3. The mechanical rod 17, provided with the reciprocating drive 18, forms calibration light pulses whose frequency and duration are determined by control electric pulses produced by electronic means (not shown) of the device for dispersion analysis of aerosols.

The diameter of the mirror 14 is selected so that the light flux it reflects should fully illuminate the diaphragm 16. The diameter of the mirror 15 is somewhat in excess of the cross-sectional dimension of the light flux separated by the diaphragm 16.

The amplitude of calibration light pulses is determined by the aperture diameter of the diaphragm 16. The stroke length of the rod 17 is selected so that the aperture of the diaphragm 16 is fully closed with the rod 17 in one extreme position, and fully opened with the rod 17 in the opposite extreme position.

With the closed aperture of the diaphragm 16, the converter detects particles contained in the aerosol flow and measures their sizes, which means it operates in the measuring mode. With the open aperture of the diaphragm 16, a predetermined part of the light flux of the illumination means 3 is applied to the input of the photoreceiver 4, which means the converter operates in the calibration mode. The electronic means incorporated in the device for dispersion analysis of aerosols separate calibration pulses from electric pulses produced as a result of conversion of light scattered by individual particles contained in the aerosol flow. As this takes place, the detection of particles and particle size measurements are discontinued.

The reciprocating drive is controlled by a pulse voltage generator which also synchronizes operation of the electronic components of the device for dispersion analysis of aerosols. The frequency, amplitude and duration of calibration light pulses are selected so that their volt-second area should be much greater than the total volt-second area of all particles detected in the course of the analysis.

The sensitivity calibration may be carried out prior to taking measurements. In such a case, the electronic means of the device for dispersion analysis of aerosols generate an electric pulse which produces a calibration light pulse before the measurement is started. From the output of the photoelectric converter, the electric calibration signal of a magnitude proportional to that of the calibration light pulse is applied to the electronic means of the device for dispersion analysis of aerosols to be stored there over the entire course of measurements.

What is claimed is:

1. A photoelectric converter of sizes of particles contained in a flow of gas to electric pulses, comprising:
a chamber;
a means for directing an aerosol flow into and from said chamber, mounted on said chamber;
an illumination means having an optical axis, optically connected to said chamber and intended to form a convergent light flux to illuminate the aerosol flow;
a photoreceiver having an optical axis, optically connected to said chamber and arranged so that its optical axis, that of said illumination means and the axis of the aerosol flow all intersect at a right angle inside said chamber;
a first mirror arranged in said chamber across said optical axis of said illumination means beyond the point of intersection of that axis with said optical axis of said photoreceiver;

a second mirror arranged in said chamber across said optical axis of said photoreceiver beyond the point of intersection of that axis with said optical axis of said illumination means;

said first and second mirrors comprising a channel for transmitting part of the light flux of said illumination means; and a calibration light pulse former, accommodated in said channel for transmitting part of the light flux of said illumination means;

said calibration light pulse former comprising:

a mechanical shutter constructed as a rod and interposed between said first and second mirrors across the path of the light flux, a diaphragm interposed between said first and second mirrors across the path of the light flux, and a reciprocating drive for driving said mechanical shutter.

* * * * *